United States Patent [19]
Neuss et al.

[11] 3,954,773
[45] May 4, 1976

[54] 4-DESACETOXYVINBLASTINE

[75] Inventors: Norbert Neuss; Albert J. Barnes, both of Indianapolis, Ind.

[73] Assignee: Eli Lilly and Company, Indianapolis, Ind.

[22] Filed: Nov. 21, 1974

[21] Appl. No.: 525,712

[52] U.S. Cl. .................. 260/286 R; 260/287 B; 424/262
[51] Int. Cl.² ............... C07D 471/18; C07D 471/22
[58] Field of Search .................. 260/287 B

[56] References Cited
UNITED STATES PATENTS
3,392,173  7/1968  Hargrove .................. 260/287 B

*Primary Examiner*—Alton D. Rollins
*Assistant Examiner*—David E. Wheeler
*Attorney, Agent, or Firm*—James L. Rowe; Everet F. Smith

[57] ABSTRACT

4-Desacetoxyvinblastine, a novel indole-dihydroindole alkaloid obtained in small quantities from *Vinca rosea*, intermediate for the preparation of antimitotic compounds.

4 Claims, No Drawings

4-DESACETOXYVINBLASTINE

BACKGROUND OF THE INVENTION

Several naturally-occurring alkaloids obtainable from *Vinca rosea* have been found active in the treatment of experimental malignancies in animals. Among these are leurosine (U.S. Pat. No. 3,370,057), vincaleukoblastine (vinblastine or VLB) (U.S. Pat. No. 3,097,137), leurosidine (vinrosidine) and leurocristine (VCR or vincristine) (both in U.S. Pat. No. 3,205,220). Two of these alkaloids, VLB and vincristine, are now marketed as drugs for the treatment of malignancies, particularly the leukemias and related diseases, in humans. Of these marketed compounds, vincristine is a most active and useful agent in the treatment of leukemias but is also the least abundant of the anti-neoplastic alkaloids of *Vinca rosea*.

Other dimeric indole alkaloids which have been isolated from *Vinca rosea* but which are less active antimitotically than VLB and vincristine include leurocolumbine, vincadiolene, leuroformine and isoleurosine (deoxy VLB "B").

SUMMARY OF THE INVENTION

This invention provides a novel indole-dihydroindole alkaloid, 4-desacetoxyvinblastine, having the following physical and chemical characteristics: melting point = 183°–190°C. with decomposition after recrystallization from methanol; $[\alpha]_D^{26} = +95.3°$ (chloroform); molecular ion M+ = 752, corresponding to an empirical formula $C_{44}H_{56}N_4O_7$.

Analysis Calcd. for: $C_{44}H_{56}N_4O_7$ ;
Analysis Calc.: C, 70.19; H, 7.50; N, 7.44; O, 14.87
Found: C, 69.71; H, 7.47; N, 7.08; O, 15.00

4-Desacetoxyvinblastine was converted to the corresponding 18'-descarbomethoxy hydrazide by the procedure used to prepare 18'-descarbomethoxy VLB hydrazide — Neuss, Huckstep and Cone, *Tetrahedron Letters*, 91, 811 (1967). 18'-descrabomethoxy-4-desacetoxyvinblastine hydrazide melted at 202°–7°C. with decomposition after recrystallization from a methylenedichloride-methanol solvent mixture as a methanol solvate. Mass spectroscopy gave a molecular ion M+ = 694.4209; calculated for $C_{41}H_{54}N_6O_4$, 694.4206.

Analysis Calcd. for: $C_{41}H_{54}N_6O_4 \cdot CH_3OH$;
Analysis Calc.: C, 69.39; H, 8.14; N, 11.56; Found: C, 69.73; H, 7.80; N, 11.51.

Acetylation of 4-desacetoxyvinblastine at the C-3 hydroxyl (under conditions which do not affect the C-4' hydroxyl — see *Tetrahedron Letters*, 91, 811 (1967)) produced 4-desacetoxyvinblastine 3-acetate, in analogy to VLB 3-acetate. A comparison of chemical shifts in the acetylmethyl signals in the nmr spectrum between VLB, its 3-acetate, 4-desacetoxyvinblastine and its 3-acetate further supported the following proposed structure for 4-desacetoxyvinblastine:

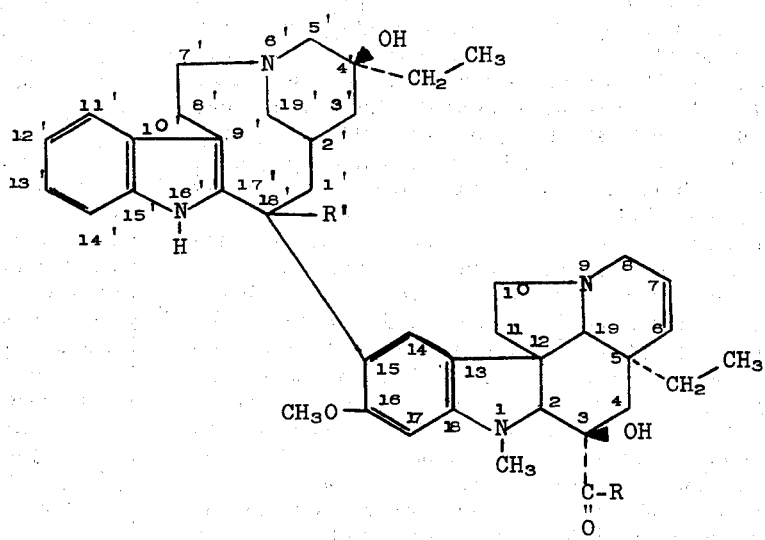

wherein R is $OCH_3$ and R' is

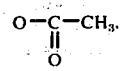

18'-Descarbomethoxy-4-desacetoxy vinblastine hydrazide, also included within the scope of this invention, is represented by the above formula when R is NH—NH₂ and R' is H.

4-Desacetoxyvinblastine forms pharmaceutically-acceptable salts with non-toxic mineral acids such as sulfuric, hydrochloric, hydrobromic, phosphoric and the like acids. Treatment of a solution of 4-desacetoxyvinblastine in anhydrous ethanol with 1 percent ethanolic sulfuric acid yields 4-desacetoxyvinblastine sulfate, an amorphous powder.

4-Desacetoxyvinblastine is prepared according to the following procedure: Leaves of plants containing crude vinca alkaloids; i.e., *Catharanthus roseus* (*Vinca rosea*), previously moistened with aqueous ammonia, are extracted with a water-immiscible solvent such as benzene. The benzene is distilled from the extract in the presence of aqueous tartaric acid. The tartaric acid layer is extracted with a water-immiscible organic solvent and is then made basic by the addition of ammonia. The dimeric alkaloids are then extracted from the alkaline layer into an organic solvent, customarily benzene. Evaporation of the benzene yields a mixture of amorphous dimeric alkaloids which are dissolved in benzene and chromatographed over alumina (CAMAG — Activity III).

The alkaloids are eluted in the following order: leurosine, VLB, des-N-methyl VLB, vincristine and vinrosidine. Identification of the dimeric alkaloids in the eluant fraction is carried out by standard procedures known to the art, as by thin layer chromatography. VLB is customarily eluted with a benzene-chloroform (1:1) solvent mixture. The procedure for obtaining the VLB fraction is more fully set forth in U.S. Pat. No. 3,225,030.

VLB fractions thus obtained were shown by thin layer chromatography to contain small quantities of a second alkaloid, later identified as 4-desacetoxyvinblastine. This second alkaloid was isolated as follows: The VLB fraction was converted to the corresponding sulfate salt by standard procedure. 200 g. of sulfates were subjected to a gradient pH separation procedure in which the sulfates were dissolved in 4 l. of 2 percent aqueous citric acid, and the citric acid solution extracted twice with 4 l. of benzene. The pH was then raised to pH = 5.5 by the addition of ammonia and two more 4 l. benzene extractions carried out. The first of these (252 C) weighed 79.2 g. and the second (242 D) weighed 42.9 g. 33 Grs. of the second fraction were chromatographed over 1020 g. of alumina (activity III) in a 2 inch outer diameter glass column. The alkaloid fraction was dissolved in 125 ml. of benzene, and the chromatogram developed with benzene. Fractions 1–3 eluted with 8.3 l. of benzene and fractions 4–13 eluted with 2 l. of a 1:3 chloroform-benzene solvent mixture contained no alkaloid. Fractions 14–15 eluted with 500 ml. portions of the same solvent mixture and fractions 16, 17, 18, 19, 20 21A and 21B eluted with 200 ml. portions of the same solvent mixture were shown by thin layer chromatography to have a second material in addition to VLB. These fractions were combined (total weight = 4.60 g.). The chromatography was repeated with 79.2 g. of the first pH = 5.5 fraction from the gradient separation procedure. This fraction in 300 ml. of benzene was chromatographed over 1050 g. of alumina (activity III). Fraction 1 eluted with 2 l. of benzene was discarded and fractions 2–4, each eluted with 150 ml. of benzene, again shown by thin layer chromatography to contain a second spot in addition to VLB, were combined (total weight = 14.6 g.). All the above fractions were combined (total weight = 19.2 g.), dissolved in 750 ml. of benzene and rechromatographed over 600 g. of alumina (activity III). A fore cut of 3 l. of benzene and cuts 1–4 employing a total of 1600 ml. of a (1:3) chloroform-benzene solvent mixture were discarded. Cuts 5–18 each eluted with 100 ml., cuts 19–21 each eluted with 200 ml., cut 22 eluted with 250 ml. and cuts 23–24, each eluted with 500 ml., of the above solvent mixture, were combined (total weight = 7.0 g.).

Crystallization from methanol of 3 g. of the combined cuts 5–24 yielded 1.52 g. of a new dimeric alkaloid, different from VLB. 500 Mg. of the new dimeric alkaloid were further purified from residual traces of VLB by chromatography over 25 g. of silica using a 3:2:4 diethylamine-chloroform-benzene solvent mixture as the eluant. The first 36 ml. of eluate were discarded. Fractions of 3 ml. each were then collected. Fractions 5–8 were combined (total weight = 320 mg.) to yield a pure dimeric alkaloid which proved to be 4-desacetoxyvinblastine having the physical and chemical characteristics set forth above.

4.14 G. of combined cuts 5–24 were converted to the sulfate salt with 1 percent ethanolic sulfuric acid in ethanol solution.

Other salts, including salts with inorganic anion such as chloride, bromide, phosphate, nitrate and the like as well as salts with organic anions such as acetate, chloroacetate, trichloroacetate, benzoate, alkyl or aryl sulfonates and the like, are prepared from the 4-desacetoxyvinblastine free base of this invention by a procedure analogous to that set forth above for the preparation of the sulfate salt by substituting the appropriate acid in a suitable diluent in place of 1 percent ethanolic sulfuric acid.

18′-Descarbomethoxy-4-desacetoxyvinblastine hydrazide was prepared by reacting 4-desacetoxyvinblastine and hydrazine in boiling ethanol. The compound melted at 202°–7°C. with decomposition after recrystallization from a methylenedichloridemethanol solvent mixture and had the physical characteristics set forth above.

The compounds of this invention, 4-desacetoxyvinblastine and 18′-descarbomethoxy-4-desacetoxyvinblastine hydrazide, are useful as starting materials or as intermediates in the preparation of anti-tumor compounds. For example 4-desacetoxyvinblastine can be converted to 4desacetoxyvinblastine C-3 carboxhydrazine by the procedure disclosed in Cullinan and Gerzon, application Ser. No. 446,869 filed Feb. 28, 1974 now abandoned and in Ser. No. 539,681, filed Jan. 9, 1975, for the preparation of the corresponding 4-desacetyl hydrazide of VLB. This procedure involves a reaction with hydrazine in ethanol solution in a sealed reaction vessel. 4-Desacetoxyvinblastine C-3 hydrazide thus prepared can be converted to the azide by reaction with sodium nitrite in acidic methanol, as disclosed by Cullinan and Gerzon, loc. cit, for the preparation of 4-desacetyl VLB C-3 carboxazide. Reaction of the C-3 carboxazide of 4-desacetoxyvinblastine with ethanolamine in methylenedichloride solution yields 4-desacetoxyvinblastine C-3 N-(2-hydroxyethyl) carboxamide, isolated as the sulfate salt. This latter compound showed marked activity against transplanted tumors in mice; specifically against Gardner lymphosarcoma at dose levels of 0.75 to 1.5 mg/kg of mouse weight when administered for 6 days after tumor inoculation and against Ridgeway osteogenic sarcoma at a dose level of 0.5 mg/kg of mouse weight administered for 10 days after tumor inoculation. Similarly, 18′-descarbomethoxy-4-desacetoxyvinblastine C-3 carboxhydrazide can be transformed to the corresponding carboxazide with sodium nitrite and the azide reacted with primary amines such as methylamine, ethylamine, β-hydroxyethylamine and the like to yield useful anti-tumor drugs.

We claim:

1. A compound of the formula

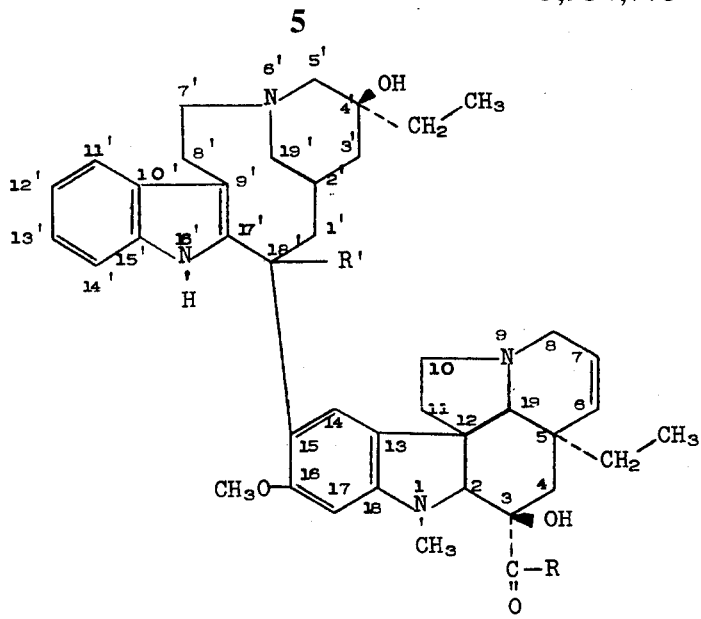
wherein R and R' are OCH₃ and
respectively or are NH—NH₂ and H, respectively.
2. The compound 4-desacetoxyvinblastine and pharmaceutically acceptable salts thereof.
3. A compound according to claim 1, said compound being 18'-descarbomethoxy-4-desacetoxyvinblastine hydrazide.
4. A sulfate salt of a compound according to claim 2.
* * * * *